(12) United States Patent
Gupta et al.

(10) Patent No.: US 10,673,415 B2
(45) Date of Patent: Jun. 2, 2020

(54) TECHNIQUES FOR GENERATING MULTIPLE LOW NOISE REFERENCE VOLTAGES

(71) Applicant: Analog Devices Global Unlimited Company, Hamilton (BM)

(72) Inventors: Gaurav Gupta, Bangalore (IN); Arthur J. Kalb, Santa Clara, CA (US)

(73) Assignee: Analog Devices Global Unlimited Company, Hamilton (BM)

( * ) Notice: Subject to any disclaimer, the term of this patent is extended or adjusted under 35 U.S.C. 154(b) by 148 days.

(21) Appl. No.: 16/048,860

(22) Filed: Jul. 30, 2018

(65) Prior Publication Data

US 2020/0036366 A1 Jan. 30, 2020

(51) Int. Cl.
| | |
|---|---|
| *A61B 5/00* | (2006.01) |
| *H03K 3/011* | (2006.01) |
| *H03K 17/60* | (2006.01) |
| *A61B 5/0428* | (2006.01) |
| *G05F 1/567* | (2006.01) |

(52) U.S. Cl.
CPC .......... *H03K 3/011* (2013.01); *A61B 5/04284* (2013.01); *A61B 5/7203* (2013.01); *G05F 1/567* (2013.01); *H03K 17/602* (2013.01); *A61B 2560/0214* (2013.01)

(58) Field of Classification Search
CPC .... A61B 2560/0209; A61B 2560/0214; A61B 5/04284; A61B 5/7203; G05F 1/567; H03K 17/602; H03K 3/011
See application file for complete search history.

(56) References Cited

U.S. PATENT DOCUMENTS

| | | | |
|---|---|---|---|
| 4,435,655 A | 3/1984 | Hauser | |
| 4,460,865 A | 7/1984 | Bynum et al. | |
| 4,618,816 A | 10/1986 | Monticelli | |
| 4,748,420 A | 5/1988 | Metz | |
| 5,180,967 A | 1/1993 | Yamazaki | |
| 5,349,286 A | 9/1994 | Marshall et al. | |
| 5,448,158 A | 9/1995 | Ryat | |

(Continued)

*Primary Examiner* — George Manuel
(74) *Attorney, Agent, or Firm* — Schwegman Lundberg & Woessner, P.A.

(57) ABSTRACT

Techniques to generate two separate temperature independent reference voltages. The reference voltages can be generated using a chain of $\Delta V_{BE}$ cells. A cross-quad $\Delta V_{BE}$-cell-based bandgap voltage reference can cancel out noise of associated current sources by forcing them to correlate. Several $\Delta V_{BE}$ stages can be cascaded together to generate an appreciable PTAT component that can cancel the CTAT component from $V_{BE}$. In some example configurations, only BJTs are used—without requiring use of an amplifier—to generate the bandgap voltages; in this way, extremely low noise voltage references can be generated. The PTAT and the CTAT voltages can be combined to generate a bandgap voltage of approximately $V_{G0}$ or approximately $2V_{G0}$.

20 Claims, 4 Drawing Sheets

(56) References Cited

U.S. PATENT DOCUMENTS

| | | | |
|---|---|---|---|
| 5,614,850 | A | 3/1997 | Corsi et al. |
| 6,002,293 | A | 12/1999 | Brokaw |
| 6,232,829 | B1 | 5/2001 | Dow |
| 7,088,085 | B2 | 8/2006 | Marinca |
| 8,228,052 | B2 | 7/2012 | Marinca |
| 8,421,433 | B2 | 4/2013 | Vyne |
| 8,508,211 | B1 | 8/2013 | Anderson |
| 9,285,820 | B2 | 3/2016 | Kalb et al. |
| 2001/0033192 | A1 | 10/2001 | Knierim et al. |
| 2004/0095186 | A1 | 8/2004 | Bernard |
| 2005/0001605 | A1 | 1/2005 | Marinca |
| 2005/0088163 | A1 | 4/2005 | Tachibana et al. |
| 2008/0007243 | A1 | 1/2008 | Matsumoto et al. |
| 2009/0039861 | A1 | 2/2009 | Wang |
| 2009/0121698 | A1 | 5/2009 | Harvey |
| 2009/0302823 | A1 | 12/2009 | Chao et al. |
| 2010/0271144 | A1* | 10/2010 | McCorquodale ........ H03B 5/04 331/117 FE |
| 2011/0241646 | A1 | 10/2011 | Vyne |
| 2013/0033245 | A1 | 2/2013 | Wong |

\* cited by examiner

TECHNIQUES FOR GENERATING MULTIPLE LOW NOISE REFERENCE VOLTAGES

FIELD OF THE DISCLOSURE

This document pertains generally, but not by way of limitation, to integrated circuits, and more particularly, to voltage reference circuits.

BACKGROUND

Within the field of semiconductor circuits, certain categories of circuitry require a reliable operation over a range of temperatures. One circuit that may be used to provide a constant reference source is a bandgap voltage reference.

Bandgap voltage reference circuits are designed to sum two voltages with opposite temperature slopes. One of the voltages is a Complementary-To-Absolute Temperature (CTAT) voltage typically provided by a base-emitter voltage ($V_{BE}$) of a forward biased bipolar transistor. The other is a Proportional-To-Absolute Temperature (PTAT) voltage typically derived from the base-emitter voltage differences of two bipolar transistors operating at different collector current densities. When the PTAT voltage and the CTAT voltage are summed together, the summed voltage is at a first order temperature insensitive.

SUMMARY OF THE DISCLOSURE

This disclosure describes techniques that can generate two separate temperature independent reference voltages. The reference voltages can be generated using a chain of $\Delta V_{BE}$ cells. A cross-quad $\Delta V_{BE}$-cell-based bandgap voltage reference can cancel out noise of associated current sources by forcing them to correlate. Several $\Delta V_{BE}$ stages can be cascaded together to generate an appreciable PTAT component that can cancel the CTAT component from $V_{BE}$. In some example configurations, only BJTs are used-without requiring use of an amplifier—to generate the bandgap voltages; in this way, extremely low noise voltage references can be generated. The PTAT and the CTAT voltages can be combined to generate a bandgap voltage of approximately $V_{G0}$ or approximately $2V_{G0}$.

In some aspects, this disclosure is directed to a voltage reference circuit to generate at least a first reference voltage and a second reference voltage. The circuit comprises a plurality of cascaded $\Delta V_{BE}$ stages, each $\Delta V_{BE}$ stage including four bipolar junction transistors (BJTs) connected in a cross-quad configuration, each $\Delta V_{BE}$ stage arranged to generate a proportional to absolute temperature (PTAT) voltage, the plurality of $\Delta V_{BE}$ stages cascaded such that their PTAT voltages are summed; a first reference voltage stage cascaded within the plurality of $\Delta V_{BE}$ stages, the first reference voltage arranged to offset a complementary to absolute temperature (CTAT) voltage with a first sum of PTAT voltages to provide the first reference voltage; and a second reference voltage stage cascaded within the plurality of $\Delta V_{BE}$ stages, the second reference voltage stage coupled to the summed PTAT voltages, the second reference voltage stage arranged to generate multiple $V_{BE}$ voltages that are summed with a second sum of PTAT voltages to provide the second reference voltage.

In some aspects, this disclosure is directed to a method of generating at least a first reference voltage and a second reference voltage. The method comprises cascading a plurality of $\Delta V_{BE}$ stages, each $\Delta V_{BE}$ stage including four bipolar junction transistors (BJTs) connected in a cross-quad configuration; generating, at each $\Delta V_{BE}$ stage, a proportional to absolute temperature (PTAT) voltage and summing the PTAT voltages of the plurality of cascaded $\Delta V_{BE}$ stages; offsetting, using a first reference voltage stage, a complementary to absolute temperature (CTAT) voltage with a first sum of PTAT voltages to provide the first reference voltage; generating multiple $V_{BE}$ voltages, using a second reference voltage stage cascaded within the plurality of $\Delta V_{BE}$ stages; and summing the multiple $V_{BE}$ voltages with a second sum of PTAT voltages to provide the second reference voltage.

In some aspects, this disclosure is directed to a voltage reference circuit to generate at least a first reference voltage and a second reference voltage. The circuit comprises a plurality of cascaded $\Delta V_{BE}$ stages, each $\Delta V_{BE}$ stage including four bipolar junction transistors (BJTs) connected in a cross-quad configuration; at each $\Delta V_{BE}$ stage, means for generating a proportional to absolute temperature (PTAT) voltage and means for summing the PTAT voltages of the plurality of cascaded $\Delta V_{BE}$ stages; means for offsetting a complementary to absolute temperature (CTAT) voltage with a first sum of PTAT voltages to provide the first reference voltage; means for generating multiple $V_{BE}$ voltages; and means for summing the multiple $V_{BE}$ voltages with a second sum of PTAT voltages to provide the second reference voltage.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A bandgap voltage reference is a type of voltage reference circuit having a low or zero temperature coefficient (TC). The low TC is achieved by generating a voltage having a positive TC, or Proportional-To-Absolute Temperature (PTAT) voltage, and summing it with a voltage having a negative TC, or Complementary-To-Absolute Temperature (CTAT) voltage, to create a reference voltage with a first-order zero TC.

In an approach to generating a bandgap reference voltage, an amplifier can provide equal currents to two bipolar junction transistors (BJTs) Q1 and Q2.

However, the current densities of Q1 and Q2 are intentionally made different, e.g., by emitter area scaling or current scaling, such that the base-emitter voltages ($V_{BE}$) for the two transistors are different. This difference, or $\Delta V_{BE}$, is a PTAT voltage that appears across a resistor. It can be gained and summed with the $V_{BE}$ of Q1, which is a CTAT voltage, to generate a reference voltage $V_{REF}$, which is given by Equation (1):

$$V_{REF} = V_{BE,Q1} + G*V_{PTAT} = G1*V_{BE,Q1} + G2*k*T/q*\ln(N),\qquad \text{Equation (1)}$$

where G1 is the $V_{BE}$ gain, G2 is the PTAT gain, k is Boltzmann's constant, T is the temperature in Kelvin, q is the charge of an electron, and N is the ratio of the current densities. The gain, G, can be arranged such that the total temperature dependence is small. The ratio of current densities of Q1 and Q2 can be altered by changing the relative emitter areas, scaling the relative collector currents, or both.

A voltage reference circuit capable of providing ultra-low noise performance is described in commonly assigned U.S. Pat. No. 9,285,820 to Kalb et al., titled "Ultra-low Noise Voltage Reference Circuit" and filed on Feb. 1, 2013, the entire contents of which being incorporated herein by reference. In U.S. Pat. No. 9,285,820, the voltage reference circuit included a plurality of ΔVBE cells, each including four bipolar junction transistors (BJTs) connected in a cross-quad configuration and arranged to generate a ΔVBE voltage. The plurality of ΔVBE cells are stacked such that their ΔVBE voltages are summed. A last stage is coupled to the summed ΔVBE voltages. The last stage is arranged to generate a VBE voltage which is summed with the ΔVBE voltages to provide a reference voltage. This arrangement serves to cancel out the first-order noise and mismatch associated with the two current sources present in each ΔVBE cell, such that the present voltage reference circuit provides ultra-low 1/f noise in the bandgap voltage output.

A low noise signal path can benefit from low noise voltage references. A higher reference voltage value can be desirable for higher dynamic range signals whereas a signal path with a lower reference voltage can be desirable for lower dynamic range signals. An integrated circuit die may have both kinds of signal paths present and, as such, it may be desirable to have two different reference voltages. One way to generate two reference voltages can be to generate a higher reference voltage (e.g., ~2.4V) and then generate a lower reference voltage from it through a resistor ladder. However, such a simple solution may not be desirable because of cross-coupling of noise between the two reference voltage nodes because one reference voltage is generated based on the other.

The present inventors have recognized the desirability of providing a low noise voltage reference circuit that can generate two separate reference voltages. A voltage reference circuit that can generate two separate reference voltages, as described in this disclosure, can help save power and reduce die area, and can exhibit very little cross-coupling between the two references. As such, the voltage reference circuit of this disclosure can help provide a power-efficient and low-noise reference voltage generation and distribution scheme.

The techniques of this disclosure can generate two separate temperature independent reference voltages. The reference voltages can be generated using a chain of $\Delta V_{BE}$ cells. A cross-quad $\Delta V_{BE}$-cell-based bandgap voltage reference can cancel out noise of associated current sources by forcing them to correlate. Several $\Delta V_{BE}$ stages can be cascaded together to generate an appreciable PTAT component that can cancel the CTAT component from $V_{BE}$. In some example configurations, only BJTs are used-without requiring use of an amplifier—to generate the bandgap voltages; in this way, extremely low noise voltage references can be generated. The PTAT and the CTAT voltages can be combined to generate a bandgap voltage of approximately $V_{G0}$ or approximately $2V_{G0}$.

Additional cross-quad cell stacking can be done in a single $\Delta V_{BE}$ stage to leverage a higher power supply voltage, e.g., the 5V supply, such that only two such stages can give sufficient PTAT component so as to cancel the CTAT component due to $V_{BE}$ and generate a bandgap voltage of approximately $V_{G0}$. Further stages of stacked $\Delta V_{BE}$ cells can be cascaded to generate more PTAT component so as to cancel a CTAT component due to $2*V_{BE}$ and generate approximately $2\ V_{G0}$, such as explained further below.

Figure 1:
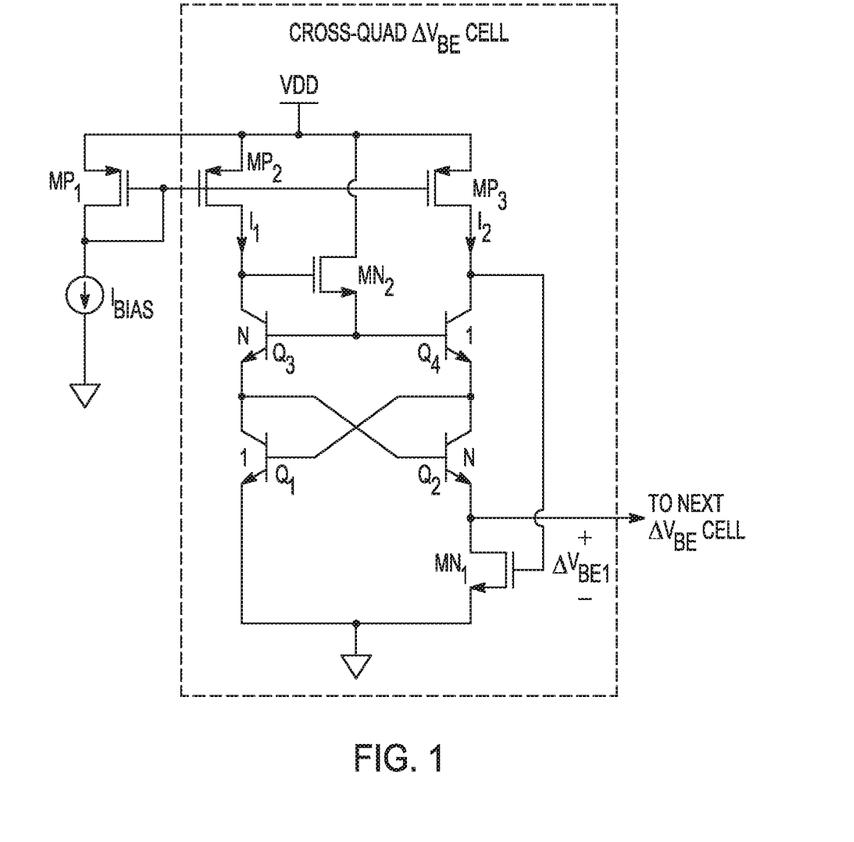
FIG. 1 is a schematic diagram of an example of a cross-quad $\Delta V_{BE}$ cell.

FIG. 1 is a schematic diagram of an example of a cross-quad $\Delta V_{BE}$ cell. The "cross-quad $\Delta V_{BE}$ cell" of FIG. 1 can cancel out to a first-order the noise and mismatch of the two current sources that provide currents $I_1$ and $I_2$. The cross-quad $\Delta V_{BE}$ cell was described in detail in commonly assigned U.S. Pat. No. 9,285,820, incorporated herein by reference including for its description of a cross-quad $\Delta V_{BE}$ cell, and for purposes of conciseness, will not be described in detail again.

Without the cross-quad connection, the current sources can be the dominant sources of noise and mismatch in the overall $\Delta V_{BE}$ output voltage. Here, however, the voltage reference provides ultra-low 1/f noise in the bandgap voltage output, making it suitable for demanding low-noise applications such as medical instrumentation. For example, one possible application is as an ultra-low-noise voltage reference for an electrocardiograph (ECG) medical application-specific standard product (ASSP).

The transistor $MN_1$, e.g., an N-type or other n-channel field-effect transistor (FET), can be employed as an active resistance across which the cell's output voltage ($\Delta V_{BE}$) appears, and transistor $MN_2$, e.g., NMOS FET, can be connected as shown to drive the bases of Q3 and Q4. In some example configurations, transistor $MN_2$ can alternatively be implemented with an NPN transistor, and that the functions provided by $MN_1$ and $MN_2$ can alternatively be provided by other means such as can include other transistors or circuitry.

In this configuration, the high-current-density transistor pair $Q_1$ and $Q_4$, e.g., Ix-sized devices, and the low-current-density transistor pair $Q_2$ and $Q_3$, e.g., Nx-sized devices, each have one NPN with a collector current originating from $I_1$ and one NPN with a collector current originating from $I_2$. The noise components introduced by $MP_2$ and $MP_3$ are forced to be correlated via the cross-quad configuration. Thus, the 1/f and wideband noise, and the mismatch of the PMOS current mirror transistors, are rejected to an amount limited only by the beta of the NPNs used in the cross-quad configuration.

Figure 2A:
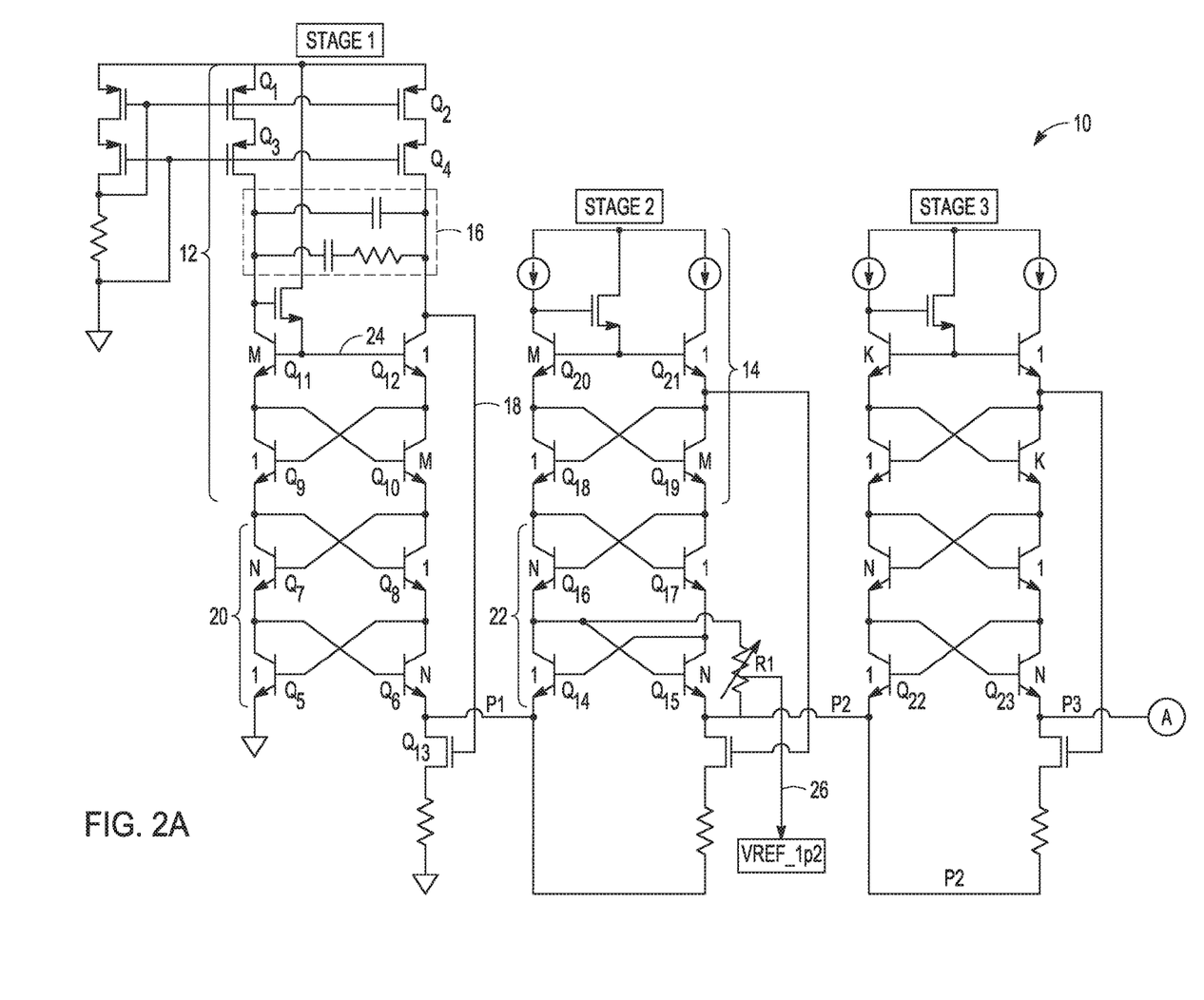
FIGS. 2A and 2B are a schematic diagram of an example of a power-efficient and low-noise reference voltage generation and distribution scheme that can generate two reference voltages, in accordance with various techniques of this disclosure.
Figure 2B:
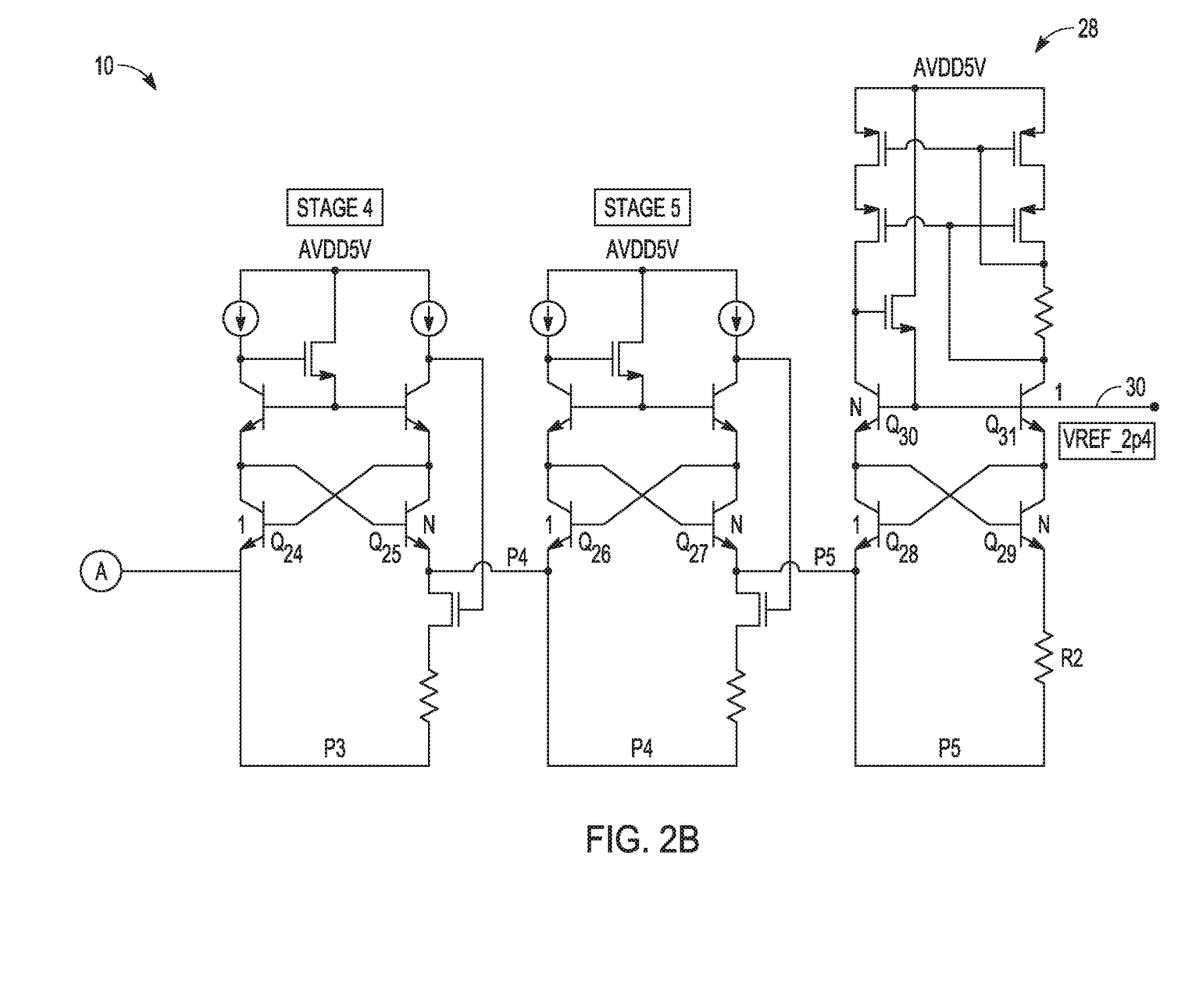

The cross-quad configuration used in the circuit of FIGS. 2A and 2B is similar to the configuration shown in FIG. 1.

FIGS. 2A and 2B are a schematic diagram of an example of a power-efficient and low-noise reference voltage generation and distribution scheme that can generate two reference voltages, in accordance with various techniques of this disclosure. As seen in FIGS. 2A and 2B, the example of a reference voltage circuit 10 can include multiple cascaded $\Delta V_{BE}$ stages, e.g., stage 1 through stage 5. As described in detail below, each $\Delta V_{BE}$ stage can be arranged to generate a $\Delta V_{BE}$ voltage and the $\Delta V_{BE}$ stages can be cascaded such that their $\Delta V_{BE}$ voltages are summed.

Each $\Delta V_{BE}$ stage, e.g., stage 1 through stage 5, can include four bipolar junction transistors (BJTs) connected in a cross-quad configuration. An example of four BJTs connected in a cross-quad configuration is shown generally at 12, with the current sources shown explicitly as transistors Q1-Q4. Another example of four BJTs connected in a cross-quad configuration is shown generally at 14. In the example configuration shown at 12, a parallel RC network 16 can be included to compensate the feedback loop 18.

At least some of the $\Delta V_{BE}$ stages can further include additional pairs of cross-coupled BJTs. For example, Stage 1 can include additional pairs of cross-coupled BJTs, as shown generally at 20, and Stage 2 can include additional pairs of cross-coupled BJTs, as shown generally at 22. In the example shown in FIGS. 2A and 2B, the BJTs forming the additional pairs can have a ratio N of emitter areas that is greater than 1. In some example configurations, the BJTs connected in a cross-quad configuration can include a ratio M of emitter areas that is greater than 1.

It should be noted that, in some examples, all low-current density transistors, e.g., Nx-sized or Mx-sized devices, can have a separate scaling. Further, the low-current density transistors, e.g., Nx-sized or Mx-sized devices, do not need to be in pairs of ratios, e.g., N on one side and N on the other side of the cross-quad configuration. Similarly, all high-current density transistors, e.g., Ix-sized devices, can have a separate scaling.

In some examples, M does not equal N. For example, in a non-limiting illustrative configuration, the emitter ratios can be chosen such that M=14 and N=24 in stages 1 and 2 so that the PTAT component cancels the CTAT component at the end of Stage 2, resulting in a reference voltage Vref_1p2 with approximately a first-order zero temperature coefficient at the end of Stage 2. The actual reference value realized is approximately the band-gap voltage of silicon. As described below, the voltage reference Vref_1p2 can optionally be amplified through a non-inverting buffer stage having a gain greater than 1. In this manner, any reference voltage value greater than the silicon bandgap voltage can be obtained and an accurate absolute trim functionality can be implemented by changing a feedback tap point, for example. It can be desirable in some configurations to select a gain as close to 1 as possible to minimize noise gain.

In some example configurations, the emitter area ratios can be selected to be different for one or more of the stages such that the PTAT and CTAT components cancel at the reference voltage outputs, e.g., first reference voltage Vref_1p2 and second reference voltage Vref_2p4. For example, in a non-limiting configuration, the emitter ratios in stage 3 can be chosen such that K=8 and N=24, while the emitter ratios in stages 1 and 2 can be chosen such that M=14 and N=24. The emitter ratios in Stage 3 can be chosen as 8 and 24 so that at the end of Stage 5, the CTAT component due to two $V_{BE}$ voltage drops cancels the summed PTAT components of Stages 1-5.

For two transistors having different current densities due to their different emitter areas and operating with the same collector current, the difference in their base emitter voltages represents $\Delta V_{BE}$, which is the PTAT voltage. For the same collector current, the difference in $V_{BE}$ for a 1× emitter area device and an N times larger (Nx) emitter area device is $\Delta V_{BE}$, which is the PTAT voltage. The $V_{BE}$ summation will now be explained. Starting from ground at the left of Stage 1, an increase of 1× $V_{BE5}$ is achieved through the base-emitter junction of BJT Q5. Another increase of 1× $V_{BE8}$ is achieved through the base-emitter junction of BJT Q8, and so forth through Q9 and Q12 until node 24 is reached.

Now, going downward from node 24, a decrease of an M times larger (Mx) emitter area transistor $V_{BE,Q11}$ (a smaller $V_{BE}$ than $V_{BE,Q12}$) is achieved through the base-emitter junction of BJT Q11. Another decrease of $V_{BE,Q10}$ is achieved through the Mx base-emitter junction of BJT Q10. A decrease of $V_{BE,Q7}$ is achieved through the Nx base-emitter junction of BJT Q7 and another decrease of $V_{BE,Q6}$ is achieved through the Nx base-emitter junction of BJT Q6 until node P1 is reached. In this manner, a summed $\Delta V_{BE}$ voltage (or PTAT voltage) generated by Stage 1 at node P1 is equal to $4*\Delta V_{BE}$, or $V_{PTAT1}$. More particularly, the voltage at node P1, $V_{PTAT1}=V_{BE,Q5}+V_{BE,Q8}+V_{BE,Q9}+V_{BE,Q12}-V_{BE,Q11}-V_{BE,Q10}-V_{BE,Q7}-V_{BE,Q6}=(V_{BE,Q5}-V_{BE,Q7})+(V_{BE,Q8}-V_{BE,Q6})+(V_{BE,Q9}-V_{BE,Q11})+(V_{BE,Q12}-V_{BE,Q10})=4*\Delta V_{BE}$.

In the example configuration shown in FIG. 2A, a transistor Q13, e.g., a FET operating in its triode region, can be part of the feedback loop 18. The transistor Q13 can be feedback regulated so that the $\Delta V_{BE}$ node voltage at P1, $V_{P1}$, can be dropped across Q13 and its source-coupled resistor while maintaining the current dictated by transistor Q2.

Stage 2 is coupled to Stage 1 in a cascaded arrangement with the output of Stage 1 at node P1 being the input to Stage 2, such that the PTAT $\Delta V_{BE}$ voltages of Stages 1 and 2 are summed. Similar to Stage 1, the transistors Q14-Q21 in Stage 2 can generate a summed $\Delta V_{BE}$ voltage (or PTAT voltage) equal to $4*\Delta V_{BE}$, or $V_{PTAT2}$, between node P1 and the emitter of transistor Q15. More particularly, $V_{PTAT2}=V_{BE,Q14}+V_{BE,Q17}+V_{BE,Q18}+V_{BE,Q21}-V_{BE,Q20}-V_{BE,Q19}-V_{BE,Q16}-V_{BE,Q15}=(V_{BE,Q14}-V_{BE,Q16})+(V_{BE,Q17}-V_{BE,Q15})+(V_{BE,Q21}-V_{BE,Q19})+(V_{BE,Q18}-V_{BE,Q20})=4*\Delta V_{BE}$. Thus, with Stages 1 and 2 cascaded, a summed $\Delta V_{BE}$ voltage (or PTAT voltage) of $V_{PTAT1}+V_{PTAT2}=8*\Delta V_{BE}$ can be generated at the emitter of the Nx BJT Q15 (node labeled as P2), and a CTAT voltage is generated across the adjustable resistor R1 using the $V_{BE,Q15}$ of the Nx BJT Q15. Summed $\Delta V_{BE}$ voltages (or PTAT voltages) can be similarly generated for Stage 3 ($V_{PTAT3}$), Stage 4 ($V_{PTAT4}$), and Stage 5 ($V_{PTAT5}$).

In some examples, a resistive element R1 can be coupled in series with the summed $\Delta V_{BE}$ voltage (or PTAT voltage) of cascaded $\Delta V_{BE}$ stages, e.g., of stages 1 and 2. The resistive element R1 can have a resistance across which a CTAT voltage can be generated and placed in series with a summed $\Delta V_{BE}$ voltage (or PTAT voltage) of $8*\Delta V_{BE}$ to provide a first reference voltage Vref_1p2. By summing the PTAT and CTAT voltages and by adjusting the resistive element R1, the PTAT and CTAT voltages can cancel each other and a temperature independent first reference voltage can be generated at output node 26, e.g., at the bandgap voltage of silicon. The resistance of resistive element R1 can be adjusted, such as by using laser trimming, on-chip digital selection, tap selection, or using one or more other adjustment techniques.

In the example configuration shown in FIGS. 2A and 2B, the actual reference value realized, or output at node 26, is slightly less than the bandgap voltage value. This can be done so that the unbuffered reference voltage can be amplified through a non-inverting buffer stage, e.g., buffer circuit 46 in FIG. 3 having a gain greater than 1. In this manner, any reference voltage value near the bandgap voltage value can be obtained and an accurate absolute trim functionality can be implemented by changing the feedback tap point at the output of the buffer circuit 46.

The resistive element R1 coupled across the base emitter junction of the BJT Q15 with an emitter area of N allows only an adjustable fraction of the CTAT $V_{BE}$ voltage to be summed with the summed PTAT component developed at node P2 using the cascaded Stages 1 and 2 to cancel temperature dependence to a first order, resulting in a first-order zero temperature coefficient bandgap reference voltage at node Vref_1p2. The resistive element R1 can be a potentiometer having various tap points. The reference voltage Vref_1p2 is given by Equation (2):

$$V\text{ref}\_1p2 = G1*(V_{PTAT1}+V_{PTAT2})+G2*V_{BE}, \quad \text{Equation (2)}$$

where G1 is the $V_{BE}$ gain, G2 is the PTAT gain. In Equation (2), the reference voltage Vref_1p2 is a reference voltage with a first-order zero temperature coefficient. In some examples, the actual reference value realized is 1.105 and is smaller than the bandgap value $V_{G0}$ of 1.2V. The voltage $V_{BE}$ is the base emitter voltage $V_{BE,Q15}$ of the BJT Q15 with an emitter area of N and is a CTAT voltage such that it has negative temperature coefficient. The voltage $V_{PTAT1}$ is equal to $4*\Delta V_{BE}$ (from Stage 1) and $V_{PTAT2}$ is equal to $4*\Delta V_{BE}$ (from Stage 2) for a summed PTAT voltage of $8*\Delta V_{BE}$. The voltage ($V_{PTAT1}+V_{PTAT2}$) has positive temperature coefficient. A PTAT voltage is kT/q*ln (N1*N2*N3), where N1-N3 represent the current density ratios. For emitter ratios of M and N in a stage, $V_{PTAT}$=kT/q*(2*ln (M)+2*ln(N)).

The resistance of the adjustable resistive element R1 is the total resistance across $V_{BE}$, and R1=R1A+R1B is fixed (R1A and R1B not depicted). In some examples, the resistive element R1A is approximately equal to 1 Megaohm and resistive element R1B is approximately 200-300 kiloohm (R1A and R1B are not depicted). The variable G2 is programmable, such as by changing a tapping point on R1. In Equation (2), the term $G2*V_{BE}$ is approximately equal to 0.5V such that the negative slope with respect to absolute temperature (CTAT) of $V_{BE}$ cancels with the positive slope of ($V_{PTAT1}+V_{PTAT2}$).

The resistance of resistive element R1 can be large, e.g., about 1 Megaohm, so that it does not significantly alter the current into the collector of the BJT Q14 with the smaller emitter area. In Stage 2, the collector currents for the bottom-most BJT pair can differ by about 10% as some of the current meant for the collector of the BJT with the smaller emitter area is diverted to R1. The diverted current can be about 0.4 microamps at room temperature, in an illustrative example. This difference in the collector current can cause a slight dependence of Vptat2 on the finite base-collector current gain (beta) of the BJTs.

Stage 3 can be coupled to Stage 2 in a cascaded arrangement such that the $\Delta V_{BE}$ voltages of Stages 1-3 are summed. Similar to Stage 1, the circuitry in Stage 3 can generate a summed $\Delta V_{BE}$ voltage (or PTAT voltage) equal to $4*\Delta V_{BE}$. A summed $\Delta V_{BE}$ voltage (or PTAT voltage) of $12*\Delta V_{BE}$ ($V_{PTAT1}+V_{PTAT2}+V_{PTAT3}$) is generated at the emitter of the BJT Q23 (labeled as P3).

Stage 4 can be coupled to Stage 3 in a cascaded arrangement such that the $\Delta V_{BE}$ voltages of Stages 1-3 are summed. Stages 1-3 include a stack of 4 pairs of transistors. For headroom reasons, however, Stages 4 and 5 include a stack of two pairs of transistors. As a result, the circuitry in Stage 4 can generate a summed $\Delta V_{BE}$ voltage (or PTAT voltage) equal to $2*\Delta V_{BE}$. A summed $\Delta V_{BE}$ voltage (or PTAT voltage) of $14*\Delta V_{BE}$ ($V_{PTAT1}+V_{PTAT2}+V_{PTAT3}+V_{PTAT4}$) is generated at the emitter of the Nx BJT Q25 (labeled as P4).

Stage 5 can be coupled to Stage 4 in a cascaded arrangement such that the $\Delta V_{BE}$ voltages of Stages 1-4 are summed. The circuitry in Stage 5 can generate a summed $\Delta V_{BE}$ voltage (or PTAT voltage) equal to $2*\Delta V_{BE}$. A summed $\Delta V_{BE}$ voltage (or PTAT voltage) of $16*\Delta V_{BE}$ ($V_{PTAT1}$+$V_{PTAT2}+V_{PTAT3}+V_{PTAT4}+V_{PTAT5}$) is generated at the emitter of the Nx BJT Q27 (labeled as P5).

Another reference voltage stage 28 can be cascaded within the plurality of $\Delta V_{BE}$ Stages 1-5 and, in particular, coupled to the summed $\Delta V_{BE}$ voltages at node P5. The reference voltage stage 28 is arranged to generate multiple $V_{BE}$ voltages that are summed with a sum of $\Delta V_{BE}$ voltages to provide a second reference voltage at output node 30. The output is taken from the base of transistors Q30, Q31 such that the summed $\Delta V_{BE}$ voltages of Stages 1-5 of $16*\Delta V_{BE}$ (or PTAT voltages) is summed with the two $V_{BE}$ voltages (or CTAT voltages) of the two Nx BJTs Q28, Q31 to generate the second reference voltage Vref_2p4 having a first-order zero temperature coefficient.

The second reference voltage Vref_2p4 is given by Equation (3):

$$V\text{ref}\_2p4 = V_{BE1}+V_{BE2}+V_{PTAT\_BIAS}+V_{PTAT5}+V_{PTAT4}+V_{PTAT3}+V_{PTAT2}+V_{PTAT1}, \quad \text{Equation (3)}$$

where $V_{BE1}$ is the base emitter voltage across BJT Q31; $V_{BE2}$ is the base emitter voltage across BJT Q28, $V_{PTAT\_BIAS}$ is the PTAT voltage across the resistive element R2 in the final stage 28 that generates the PTAT bias; $V_{PTAT5}$ is the PTAT voltage generated in Stage 5; $V_{PTAT4}$ is the PTAT voltage generated in Stage 4; $V_{PTAT3}$ is the PTAT voltage generated in Stage 3; $V_{PTAT2}$ is the PTAT voltage generated in Stage 2; and $V_{PTAT1}$ is the PTAT voltage generated in Stage 1. For emitter ratios of M and N in a stage, $V_{PTAT}$=kT/q*(2*ln(M)+2*ln(N)).

Figure 3:
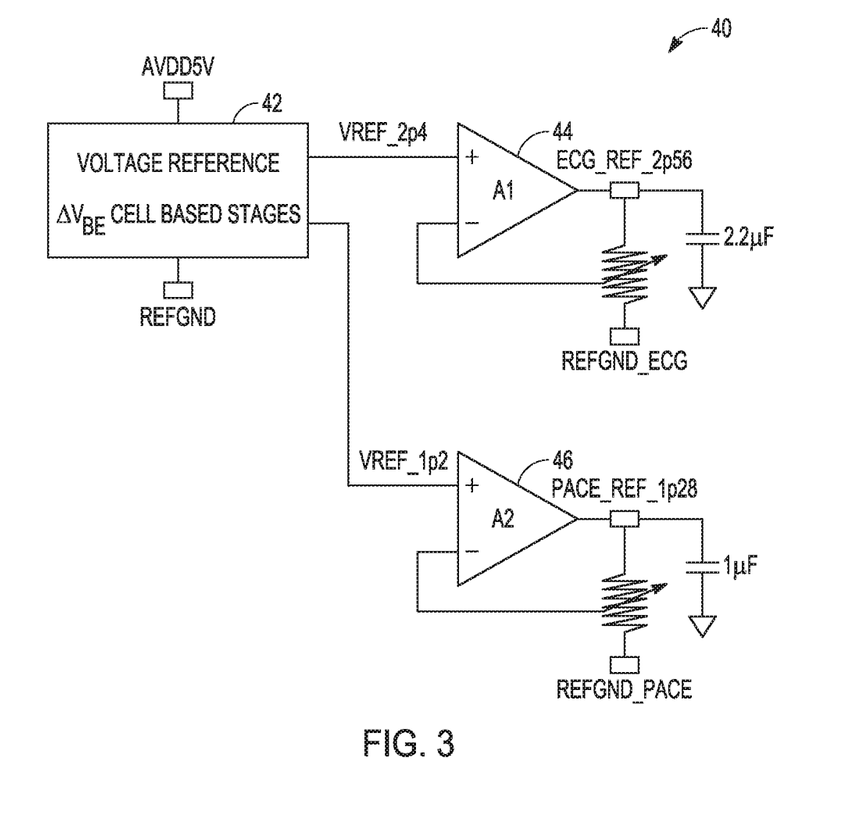
FIG. 3 is a schematic diagram of an example of a multi-channel circuit that can implement various techniques of this disclosure.

FIG. 3 is a schematic diagram of an example of a multi-channel circuit 40 that can implement various techniques of this disclosure. In some example implementations, the multi-channel circuit 40 of FIG. 3 can form a portion of an electrocardiogram (ECG) measurement circuit in combination with the voltage reference circuit 10 of FIGS. 2A and 2B. As described above, the techniques of FIGS. 2A and 2B can generate two separate temperature independent reference voltages. In FIG. 3, the multi-channel circuit 40 can include two separate reference buffers for the two separate temperature independent reference voltages.

In FIG. 3, the block 42 represents the circuitry of FIGS. 2A and 2B. The block 42 outputs two temperature independent reference voltages, namely first reference voltage Vref_1p2 and second reference voltage Vref_2p4. The circuit 40 of FIG. 3 includes two buffer circuits 44, 46. By utilizing the circuit of FIGS. 2A and 2B in block 42 in which two separate reference voltages are generated, very little cross-coupling occurs between the two buffer circuits 44, 46.

The first buffer circuit 44 receives the reference voltage Vref_2p4 and, using the feedback resistor divider network 48, can amplify the reference voltage Vref_2p4 to generate a first channel reference voltage of about 2.56V, such as for use with an ECG channel. In some example configurations, the buffer circuit 44 can be a BJT-based circuit, which can have better noise performance characteristic when compared with CMOS-based circuits.

The second buffer circuit 46 receives the reference voltage Vref_1p2 and, using the feedback resistor divider network 50, can amplify the reference voltage Vref_1p2 to generate a second channel reference voltage of about 1.28V, such as for use with a pace channel. In some example configurations, the buffer circuit 46 can be a FET-based circuit, e.g., CMOS-based. Being CMOS-based, the buffer circuit 46 will not load the second stage or disturb the current in the second stage. This can provide good crosstalk performance as the high performance 2.4V reference is not affected even if the buffer circuit 46 drives a switched capacitor or other noisy load.

Using the various techniques described above, a low noise voltage reference circuit can be provided that can generate two separate reference voltages, exhibiting very little cross-coupling between them the references. A voltage reference circuit that can generate two separate reference voltages, as described above, can save power and reduce die area, thereby providing a power-efficient and low-noise reference voltage generation and distribution scheme.

Various Notes

Each of the non-limiting aspects or examples described herein may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact discs and digital video discs), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A voltage reference circuit to generate at least a first reference voltage and a second reference voltage, the circuit comprising:

a plurality of cascaded $\Delta V_{BE}$ stages, wherein a $\Delta V_{BE}$ stage is configured to produce at least one $\Delta V_{BE}$, and wherein the at least one $\Delta V_{BE}$ is a difference between base-emitter voltages of two transistors, each $\Delta V_{BE}$ stage including four bipolar junction transistors (BJTs) connected in a cross-quad configuration, each $\Delta V_{BE}$ stage arranged to generate a proportional to absolute temperature (PTAT) voltage, the plurality of $\Delta V_{BE}$ stages cascaded such that their PTAT voltages are summed;

a first reference voltage stage cascaded within the plurality of $\Delta V_{BE}$ stages, the first reference voltage arranged to offset a complementary to absolute temperature (CTAT) voltage with a first sum of PTAT voltages to provide the first reference voltage; and a second reference voltage stage cascaded within the plurality of $\Delta V_{BE}$ stages, the second reference voltage stage coupled to the summed PTAT voltages, the second reference voltage stage arranged to generate multiple base-emitter voltages ($V_{BE}$) that are summed with a second sum of PTAT voltages to provide the second reference voltage.

2. The voltage reference circuit of claim 1, wherein at least some of the $\Delta V_{BE}$ stages further include additional pairs of cross-coupled BJTs, wherein the BJTs forming the additional pairs have a first ratio of emitter areas that is greater than 1.

3. The voltage reference circuit of claim 2, wherein the BJTs connected in a cross-quad configuration have a second ratio of emitter areas that is greater than 1.

4. The voltage reference circuit of claim 3, wherein the first and second ratios are different.

5. The voltage reference circuit of claim 1, wherein the BJTs connected in a cross-quad configuration in one of the plurality of $\Delta V_{BE}$ stages have a first ratio of emitter areas that is greater than 1, and wherein the BJTs connected in a cross-quad configuration in another of the plurality of $\Delta V_{BE}$ stages have a second ratio of emitter areas that is greater than 1, wherein the first and second ratios are different.

6. The voltage reference circuit of claim 1, wherein the first reference voltage stage includes:
a resistive element coupled between a pair of cascaded $\Delta V_{BE}$ stages, the resistive element having a resistance to offset the CTAT voltage with the first sum of PTAT voltages to provide the first reference voltage.

7. The voltage reference circuit of claim 1, wherein the resistance of the resistive element is adjustable.

8. The voltage reference circuit of claim 1, wherein the voltage reference circuit is arranged such that each of the first reference voltage and the second reference voltage have a first-order temperature coefficient of zero.

9. The voltage reference circuit of claim 1, wherein the plurality of $\Delta V_{BE}$ stages includes five cascaded $\Delta V_{BE}$ stages, and wherein the resistive element is coupled between first and second cascaded $\Delta V_{BE}$ stages.

10. The voltage reference circuit of claim 1, in combination with:
a first channel circuit including a first channel buffer circuit to receive the first reference voltage and provide a first channel reference voltage; and
a second channel circuit including a second channel buffer circuit to receive the second reference voltage and provide a second channel reference voltage.

11. The voltage reference circuit of claim 10, wherein the first channel buffer circuit is a FET-based buffer circuit, and wherein the second channel buffer circuit is a BJT-based buffer circuit.

12. The voltage reference circuit of claim 10, included in or in combination with an electrocardiogram (ECG) measurement circuit.

13. A method of generating at least a first reference voltage and a second reference voltage, the method comprising:
cascading a plurality of $\Delta V_{BE}$ stages, wherein a $\Delta V_{BE}$ stage is configured to produce at least one $\Delta V_{BE}$, and wherein the at least one $\Delta V_{BE}$ is a difference between base-emitter voltages of two transistors, each $\Delta V_{BE}$ stage including four bipolar junction transistors (BJTs) connected in a cross-quad configuration;
generating, at each $\Delta V_{BE}$ stage, a proportional to absolute temperature (PTAT) voltage and summing the PTAT voltages of the plurality of cascaded $\Delta V_{BE}$ stages;
offsetting, using a first reference voltage stage, a complementary to absolute temperature (CTAT) voltage with a first sum of PTAT voltages to provide the first reference voltage;
generating multiple base-emitter voltages ($V_{BE}$), using a second reference voltage stage cascaded within the plurality of $\Delta V_{BE}$ stages; and
summing the multiple $V_{BE}$ voltages with a second sum of PTAT voltages to provide the second reference voltage.

14. The method of claim 13, further comprising:
cross-coupling additional pairs of BJTs within at least some of the $\Delta V_{BE}$ stages, wherein the BJTs forming the additional pairs have a ratio of emitter areas that is greater than 1.

15. The method of claim 14, wherein cascading a plurality of $\Delta V_{BE}$ stages, each $\Delta V_{BE}$ stage including four bipolar junction transistors (BJTs) connected in a cross-quad configuration includes:
cascading a plurality of $\Delta V_{BE}$ stages, each $\Delta V_{BE}$ stage including four bipolar junction transistors (BJTs) connected in a cross-quad configuration and having a ratio of emitter areas that is greater than 1.

16. The method of claim 13, wherein offsetting, using the first reference voltage stage, a CTAT voltage with the first sum of PTAT voltages to provide the first reference voltage includes:
coupling a resistive element between a pair of cascaded $\Delta V_{BE}$ stages, the resistive element having a resistance to offset the CTAT voltage with the first sum of PTAT voltages to provide the first reference voltage.

17. The method of claim 16, further comprising:
adjusting the resistance of the resistive element.

18. The method of claim 13, further comprising:
receiving the first reference voltage, using a first channel circuit including a first channel buffer circuit, and generating a first channel reference voltage; and
receiving the second reference voltage, using a second channel circuit including a second channel buffer circuit, and generating a second channel reference voltage.

19. A voltage reference circuit to generate at least a first reference voltage and a second reference voltage, the circuit comprising:
a plurality of cascaded $\Delta V_{BE}$ stages, wherein a $\Delta V_{BE}$ stage is configured to produce at least one $\Delta V_{BE}$, and wherein the at least one $\Delta V_{BE}$ is a difference between base-emitter voltages of two transistors, each $\Delta V_{BE}$ stage including four bipolar junction transistors (BJTs) connected in a cross-quad configuration;
at each $\Delta V_{BE}$ stage, means for generating a proportional to absolute temperature (PTAT) voltage and means for summing the PTAT voltages of the plurality of cascaded $\Delta V_{BE}$ stages;
means for offsetting a complementary to absolute temperature (CTAT) voltage with a first sum of PTAT voltages to provide the first reference voltage;
means for generating multiple base-emitter voltages ($V_{BE}$); and
means for summing the multiple $V_{BE}$ voltages with a second sum of PTAT voltages to provide the second reference voltage.

20. The voltage reference circuit of claim 19, wherein the means for offsetting the CTAT voltage with a first sum of PTAT voltages to provide the first reference voltage includes:
means for adjusting a resistance of a resistive element coupled between a pair of cascaded $\Delta V_{BE}$ stages.

* * * * *